US010856759B2

(12) United States Patent
Bar-Tal et al.

(10) Patent No.: US 10,856,759 B2
(45) Date of Patent: Dec. 8, 2020

(54) ITERATIVE COHERENT MAPPING OF CARDIAC ELECTROPHYSIOLOGICAL (EP) ACTIVATION INCLUDING REENTRY EFFECTS

(71) Applicant: Biosense Webster (Israel) Ltd., Yokneam (IL)

(72) Inventors: Meir Bar-Tal, Haifa (IL); Alon Baram, Yokneam Ilit (IL); Avram Dan Montag, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 174 days.

(21) Appl. No.: 16/184,653

(22) Filed: Nov. 8, 2018

(65) Prior Publication Data

US 2020/0146572 A1    May 14, 2020

(51) Int. Cl.
| A61B 5/00 | (2006.01) |
| A61B 5/044 | (2006.01) |
| G16H 20/40 | (2018.01) |
| G16H 30/40 | (2018.01) |
| A61B 5/04 | (2006.01) |
| A61B 5/0464 | (2006.01) |

(52) U.S. Cl.
CPC .......... *A61B 5/044* (2013.01); *A61B 5/04012* (2013.01); *A61B 5/0464* (2013.01); *G16H 20/40* (2018.01); *G16H 30/40* (2018.01)

(58) Field of Classification Search
CPC ... A61B 5/044; A61B 5/04012; A61B 5/0464; A61B 5/743; A61B 5/0422; A61B 5/04011; A61B 5/04085; G16H 20/40; G16H 30/40
See application file for complete search history.

(56) References Cited

U.S. PATENT DOCUMENTS

| 6,301,496 B1 | 10/2001 | Reisfeld |
| 8,456,182 B2 | 6/2013 | Bar-Tal et al. |
| 9,050,011 B2 | 6/2015 | Rubinstein et al. |
| 2009/0112109 A1 | 4/2009 | Kuklik |
| 2011/0144510 A1 | 6/2011 | Ryu |
| 2014/0371833 A1 | 12/2014 | Ghosh |

(Continued)

FOREIGN PATENT DOCUMENTS

EP    1070480 A2    1/2001

OTHER PUBLICATIONS

Potra, Florian A. et al., "Interior-point methods", Journal of Computational and Applied Mathematics, (2000), pp. 281-302, vol. 124, Issue 1-2.

(Continued)

*Primary Examiner* — Scott M. Getzow

(57) ABSTRACT

A method includes receiving an input mesh representation of a cardiac chamber, a set of measured locations on a wall tissue of the cardiac chamber, and a respective set of local activation times (LATs) measured at the locations. The input mesh is re-meshed into a regular mesh including regularized polygons. The set of measured locations and respective LATs is data fitted to the regularized polygons. Respective LAT values are iteratively calculated for the regularized polygons, so as to obtain a cyclic EP activation wave solution over the regular mesh that take account of reentry of an EP wave. An electroanatomical map including the cyclic EP activation wave overlaid on the regular mesh is presented.

6 Claims, 6 Drawing Sheets

(56) References Cited

U.S. PATENT DOCUMENTS

2015/0294082 A1  10/2015  Passerini
2016/0022375 A1  1/2016  Blake
2016/0106376 A1  4/2016  Li et al.
2016/0345852 A1  12/2016  Laughner
2017/0185740 A1  6/2017  Seegerer
2017/0281031 A1  10/2017  Houben et al.

OTHER PUBLICATIONS

Trefethen, L.N., "Numerical linear algebra—Lecture 23. Cholesky Factorization", Society for Industrial and Applied Mathematics, 1997, pp. 172-178.

European Search Report for Corresponding EPA No. 19207733.7 dated Apr. 15, 2020.

Vincent Jacquemet et al., "Modeling Atrial Arrhythmias: Impact on Clinical Diagnosis and Therapies", IEEE Reviews in Biomedical Engineering, vol. 1, pp. 91-114, 2008.

Edward J. Ciaccia, Ph.D, et al., "Detection of the diastolic pathway, circuit morphology, and inducibility of human postinfarction ventricular tachycardia from magging in sinus rhythm", Heart Rhythm, vol. 5, No. 7, pp. 981-991, Jul. 2008.

Rafael Sebastian et al., "Characterization and Modeling of the Peripheral Cardiac Conduction System", IEEE Transactions on Medical Imaging, vol. 32, No. 1, pp. 45-55, Jan. 2013.

M. Potse, "Integrated electrocardiographic mapping, Combined analysis of multichannel endocardial and body surface ECG data", Ph.D thesis, Chapter 3, downloaded from UvA-DARE, the institutional repository of the Univ. of Amsterdam http://hdl.handle.net/11245/2.15500.

European Search Report for corresponding EPA No. 19207655.2 dated Apr. 2, 2020.

US 10,856,759 B2

ITERATIVE COHERENT MAPPING OF CARDIAC ELECTROPHYSIOLOGICAL (EP) ACTIVATION INCLUDING REENTRY EFFECTS

CROSS-REFERENCE TO RELATED APPLICATIONS

This application is related to a U.S. Patent Application entitled "ITERATIVE COHERENT MAPPING OF CARDIAC ELECTROPHYSIOLOGICAL (EP) ACTIVATION INCLUDING SCAR EFFECTS," filed on even date, whose disclosure is incorporated herein by reference.

FIELD OF THE INVENTION

The present invention relates generally to electrophysiological mapping, and particularly to methods and systems for cardiac electrophysiological mapping.

BACKGROUND OF THE INVENTION

Electrophysiological cardiac mapping is often used for identifying potential sources of cardiac arrhythmia in cardiac tissue. For example, U.S. Patent Application Publication 2017/0281031 describes electroanatomic mapping that carried out by inserting a multi-electrode probe into a heart of a living subject, recording electrograms from the electrodes concurrently at respective locations in the heart, delimiting respective activation time intervals in the electrograms, generating a map of electrical propagation waves from the activation time intervals, maximizing coherence of the waves by adjusting local activation times within the activation time intervals of the electrograms, and reporting the adjusted local activation times.

As another example, U.S. Patent Application Publication 2016/0106376 described computing the local conduction velocity of a cardiac activation wavefront by collecting a plurality of electrophysiology ("EP") data points using a multi-electrode catheter, with each EP data point including both position data and local activation time ("LAT") data. For any EP data point, a neighborhood of EP data points, including the selected EP data point and at least two additional EP data points, can be defined. Planes of position and LATs can then be defined using the positions and LATs, respectively, of the EP data points within the neighborhood. A conduction velocity can be computed from an intersection of the planes of positions and LATs. The resultant plurality of conduction velocities can be output as a graphical representation (e.g., an electrophysiology map), for example by displaying vector icons arranged in a uniform grid over a three-dimensional cardiac model U.S. Pat. No. 6,301,496 describes a method of diagnosing an abnormal condition in a biological structure, such as the heart, including the steps of measuring a physiological response at least three sampled points on a surface of the biological structure, calculating a vector function related to the response, displaying a representation of the vector function, and inferring the abnormal condition from the representation. The present invention is particularly useful for diagnosing cardiac arrhythmias, in which case the physiological response is a voltage, from which is inferred a local activation time and the vector function is a gradient of the local activation time, specifically, a conduction velocity. The magnitude of the conduction velocity is expected to be abnormally low in scar tissue.

SUMMARY OF THE INVENTION

An embodiment of the present invention provides a method including receiving an input mesh representation of a cardiac chamber, a set of measured locations on a wall tissue of the cardiac chamber, and a respective set of local activation times (LATs) measured at the locations. The input mesh is re-meshed into a regular mesh including regularized polygons. The set of measured locations and respective LATs is data fitted to the regularized polygons. Respective LAT values, and respective probabilities that the wall tissue includes scar tissue, are iteratively calculated for the regularized polygons, so as to obtain an electrophysiological (EP) activation wave over the regular mesh that indicates scar tissue. An electroanatomical map overlaid on the regular mesh, the map including the EP activation wave and the scar tissue, is presented.

In some embodiments, the regularized polygons include regularized triangles.

In some embodiments, iteratively calculating the LAT values and the probabilities includes iteratively solving a set of equations for the LAT values, slowness values and propagation of the EP wave.

In an embodiment, iteratively calculating the probabilities includes reassigning to each regularized polygon a slowness vector recalculated using a scar weight multiplier.

In another embodiment, the method further includes binary tagging at least some of the measured locations to indicate at least one of a presence of a scar and a presence of a double EP potential.

In some embodiments, presenting the electroanatomical map includes overlaying on the electroanatomical map conduction arrows indicative of scar tissue.

There is additionally provided, in accordance with an embodiment of the present invention, a system including an interface and a processor. The interface is configured to receive an input mesh representation of a cardiac chamber, a set of measured locations on a wall tissue of the cardiac chamber, and a respective set of local activation times (LAT) measured at the locations. The processor is configured to re-mesh the input mesh into a regular mesh including regularized polygons, data fit the set of measured locations and respective LATs to the regularized polygons, and iteratively calculate for the regularized polygons (i) respective LAT values and (ii) respective probabilities that the wall tissue includes scar tissue, so as to obtain an electrophysiological (EP) activation wave over the regular mesh that indicates scar tissue. The processor is further configured to present an electroanatomical map, including the EP activation wave and the scar tissue, overlaid on the regular mesh.

Another embodiment of the present invention provides a method including receiving an input mesh representation of a cardiac chamber, a set of measured locations on a wall tissue of the cardiac chamber, and a respective set of local activation times (LATs) measured at the locations.

The input mesh is re-meshed into a regular mesh including regularized polygons. The set of measured locations and respective LATs is data fitted to the regularized polygons. Respective LAT values are iteratively calculated for the regularized polygons, so as to obtain a cyclic EP activation wave solution over the regular mesh that take account of reentry of an EP wave. An electroanatomical map including the cyclic EP activation wave overlaid on the regular mesh is presented.

In some embodiments, iteratively calculating the LAT values includes iteratively solving a set of complex valued equations that are configured to describe the reentry of an EP wave by including a reentry cycle length value.

In some embodiments, iteratively calculating the LAT values includes iteratively solving a set of three linear equations for the LAT values, slowness values and propagation of the EP wave.

In an embodiment, iteratively calculating the LAT values includes reassigning to each regularized polygon a slowness vector recalculated using a proximity weight multiplier.

There is additionally provided, in accordance with an embodiment of the present invention, a system including an interface and a processor. The interface, is configured to receive an input mesh representation of a cardiac chamber, a set of measured locations on a wall tissue of the cardiac chamber and a respective set of local activation times (LAT) measured at the locations. The processor is configured to re-mesh the input mesh into a regular mesh including regularized polygons, data fit the set of measured locations and respective LATs to the regularized polygons, and iteratively calculate for the regularized polygons respective LAT values, so as to obtain a cyclic EP activation wave solution over the regular mesh that take account of reentry of an EP wave. The processor further is configured to present an electroanatomical map including the cyclic EP activation wave overlaid on the regular mesh.

The present invention will be more fully understood from the following detailed description of the embodiments thereof, taken together with the drawings in which:

DETAILED DESCRIPTION OF EMBODIMENTS

Overview

Figure 1:
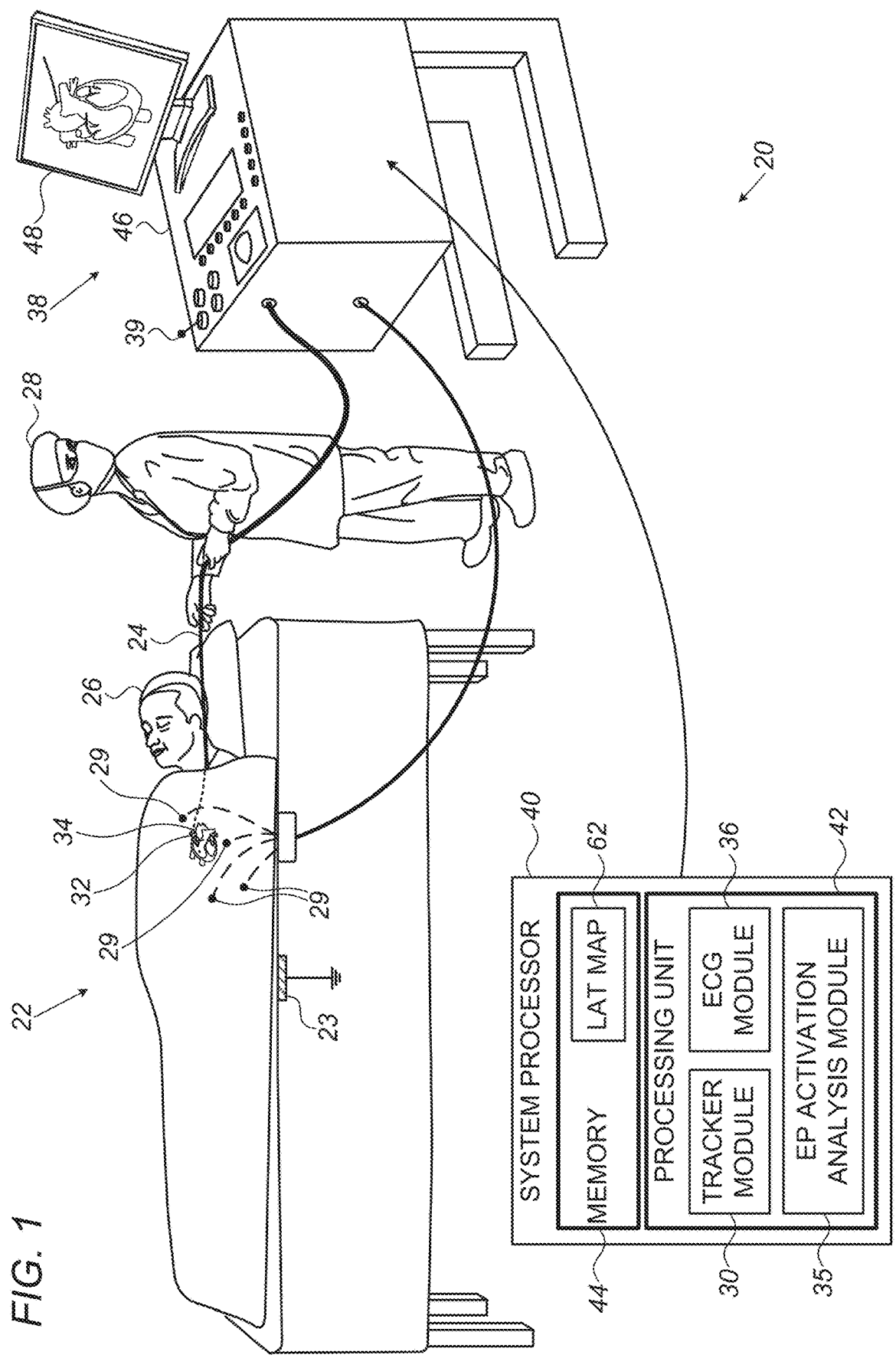
FIG. 1 is a schematic, pictorial illustration of a cardiac three-dimensional (3D) navigation and electrophysiological (EP) signal analysis system, in accordance with an embodiment of the present invention.

Cardiac arrhythmia is a class of clinical conditions in which the heartbeat is irregular. Within this class of conditions, an important group is supraventricular tachycardia (SVT), which includes atrial tachycardia, atrial fibrillation, atrial flutter, and paroxysmal supraventricular tachycardia. In SVT, as the above names suggest, the arrhythmia originates from an atrium of a heart.

Part of the SVT events are electrophysiological (EP) disruptions caused by scar tissue. For example, atypical atrial tachycardia events often develop in patients with ablation related scars. In regions of scar tissue, EP activation could be totally blocked or partially blocked (regions of slow conduction). These regions are referred to hereafter as "line of block" or scar regions.

Embodiments of the present invention that are described hereafter provide iterative coherent electroanatomical (ICEA) mapping methods and systems to identify an underlying arrythmia that belongs to the SVT group. In the context of the disclosed description, "coherent" means deriving a best-fit EP activation wave propagation description, in which conduction velocity is cyclic and continuous.

Therefore, no sharp turns in direction of an activation wave or abrupt changes in activation wave velocity are mathematically allowed, except in non-conducting areas, such as scars, where activation is blocked by certain anatomical barriers or scar tissue. Thus, in addition to correctly capturing the continuous and cyclic (i.e., activation wave reentries, as descried below) features of the cardiac EP activation, the disclosed coherent mapping method produces an EA map that shows scar regions of any form (e.g., line).

The disclosed coherent mapping method addresses, as noted above, the occurrence of activation wave reentries, such as a reentry tachycardia (RT), which is a physiological condition where the EP activation wave travels in a circle within the heart (i.e., an occurrence of a cyclic EP activation wave), rather than moving from one end of the heart to the other and then terminating over a physiological barrier (non-conducting anatomy). As the EP activation wave continuously propagates at some cycle length (e.g., a time between consecutive peaks in the ECG), wave propagation in a cardiac chamber can span the entire reentry cycle, where a wavefront "late" in the cycle meets the "early" wavefront of the next cycle. As a result, regions might be assigned wrong local activation times (LATs) that are one cycle length apart, whereas these wave-fronts should be close in time.

By taking wave reentries into account, embodiments of the disclosed ICEA method overcomes resulting reentry artifacts in an EA map and therefore ICEA is designed to work in most arrhythmia types, while, in some embodiments, the disclosed method is optimized for the atrial flutter (AFL) case and other macro-reentry cases. A resulting EA map of the cardiac chamber that typically shows aberrant EP activity, for example due to the presence of AFL, presents such aberrant EP activity in a way free of reentry-related "rainbow" artifacts (described below) that are caused otherwise, i.e., by a model not taking account of EP wave reentries. Such "rainbow" artifacts are therefore eliminated by using the disclosed ICEA mapping method.

In some embodiments, the disclosed model receives an input mesh representation of a cardiac chamber, a set of measured locations on a wall tissue of the cardiac chamber, and a respective set of LATs measured at the locations. Together, the locations and respective LAT values are also named hereinafter "data-points." The processor re-meshes the input mesh into a regular mesh comprising regularized polygons, such as triangles, which are also named hereinafter "faces." In some embodiments, the processor performs data fitting of the set of measured data-points to the regularized polygons.

After an initial iterative coherent solution is obtained, information that indicates discontinuities in the otherwise continuous ICEA map is used. For example, the processor utilizes user-provided tagging of the data-points as indicative of normal, scarred or double potential tissue regions. In the context of the disclosed description, a double EP potential is defined as a particular double spike that may be identified in fractionated and multi-component electrograms recorded on tissue wall of a cardiac chamber, such as of an atrium.

In some embodiments of the present invention, a processor further assigns each face (i.e., triangle) a probability of being an electrically non-conducting area, i.e., scar tissue. The probability is assigned (either automatically or manually by a user) by taking account of measured points on the map being normal, scarred, or double potential measurements. The assignment can also include consideration of LAT patterns and slowness values, where slowness is a vector whose magnitude is the inverse of the magnitude of the EP signal velocity vector along a geodesic connecting two neighboring faces, and whose direction is the same as the velocity vector, as described below.

Once a face has been given a high probability of being non-conducting, a relaxed slowness continuity constraint, as well as a relaxed bounding velocity constraint, are applied to generate a map that considers the possible existence of scar tissue. Areas of slow conduction (including lines of block) are further identified by activation waves with opposing vectors of propagation (i.e., anti-parallel conduction arrows on the ICEA map that indicate a line of blockage between them), where the vector of propagation goes around the scar, indicating non-conductive tissue. In an embodiment, locations with low amplitude of EP signal are assigned with a higher probability of being part of a conduction barrier.

The processor estimates, by iteratively calculating LAT values and probabilities (i.e., weights) for each face to be either conductive or part of a scarred region, an EP activation wave over the regular mesh, including indications of scarred regions. The iteratively calculated weights infer data that increase or decrease the likelihood that a certain face is a scar and outputs calculated scar probabilities for each face. The scar weights (i.e., scar probabilities) are then incorporated back in the linear equations as multiplication weights that reduce the strength of the continuity equations in line of block regions. Constraints over the slowness are reduced as well by the same multiplication weights. This allows the solution to change more freely (e.g., abruptly) in line of block regions. The processor performs the iterative calculation based on the assumption that the EP activation wave is continuous unless it encounters scar regions.

The processor then generates a coherent activation map which describes an EP activation wave which is typically at least partially aberrant, for example due to the presence of scars. In an embodiment, the processor presents a resulted ICEA map using a cyclic color scale, so as to suppress presentation dependency on "Early Meets Late," that causes the "rainbow artifact," as described below. In another embodiment, the coherent EP activation map comprises conduction arrows that illustrate normal or aberrant propagation of the EP activation wave.

Typically, the processor is programmed in software containing a particular algorithm that enables the processor to conduct each of the processor related steps and functions outlined above.

The disclosed iterative coherent EP mapping method creates a mapping system in which physicians can easily and reliably map and interpret complex arrhythmias. Thus, the disclosed systems and methods provide a tool that may increase the success rate of a subsequent invasive cardiac treatment, such as catheter ablation.

System Description

FIG. 1 is a schematic, pictorial illustration of a three-dimensional (3D) navigation and electrophysiological (EP) signal analysis system 20, in accordance with an embodiment of the present invention. System 20 may be configured to analyze substantially any physiological parameter or combinations of such parameters. In the description herein, by way of example, the signals analyzed are assumed to be intra-cardiac and/or extra-cardiac (body surface) electrocardiogram (ECG) potential-time relationships. In order to fully characterize such relationships, the signals at various locations need to be referenced in time to each other, such as is done during LAT map generation. The time referencing is accomplished by measuring relative to a reference-time (e.g., an instance in time), such as the beginning of each QRS complex of an ECG reference signal (i.e., the beginning of every heartbeat). In an embodiment, the reference signal is received from a catheter placed in the coronary sinus. For an SVT the reference signal represents the atrial activity, which may be double or triple the frequency of the ventricular activity. The method for generating an LAT map is described in U.S. Pat. No. 9,050,011, cited above.

For simplicity and clarity, the following description, except where otherwise stated, assumes an investigative procedure wherein system 20 measures actual electrical activity of a heart 34, using a probe 24. A distal end 32 of the probe is assumed to have electrodes 22. The measured signals are used, among other usages, for creating an LAT map of at least part of the wall tissue of heart 34 of a patient 26.

Typically, probe 24 comprises a catheter which is inserted into the body of patient 26 during a mapping procedure performed by a physician 28 using system 20. During the procedure patient 26 is assumed to be attached to a grounding electrode 23. In addition, electrodes 29 are assumed to be attached to the skin of patient 26, in the region of heart 34.

In an embodiment, probe 24 acquires local intra-cardiac electrocardiograms (ECG) as it being is moved over a portion of the heart chamber. Some of the features in the measured intra-cardiac ECG traces are annotated at the moment that an aberrant EP activation wave passes under a catheter electrode. At these instances probe 24 location is recorded as well.

System 20 may be controlled by a system processor 40, comprising a processing unit 42 communicating with a memory 44. In some embodiments, a memory 44, which is included in system processor 40, stores an LAT and/or voltage map 62 of at least part of wall tissue of heart 34 of patient 26. Processor 40 is typically mounted in a console 46, which comprises operating controls 38, typically including a pointing device 39 such as a mouse or trackball, that physician 28 uses to interact with the processor.

Processor 40 (specifically processing unit 42) runs software, comprising a probe tracker module 30, an ECG module 36, and an EP activation analysis module 35, to operate system 20 and/or for EP activation analysis module 35 to run the at least part of disclosed analysis (using, for example, LAT or adjusted LAT maps 62 stored in memory 44) so as to model arrhythmia.

ECG module 36 is coupled to receive actual electrical signals from electrodes 22 and electrodes 29. The module is configured to analyze the actual signals and may present the results of the analysis in a standard ECG format, typically a graphical representation moving with time, on a display 48.

Probe tracker module 30 typically tracks the location of distal end 32 of probe 24, within the heart of patient 26. The tracker module may use any method for location tracking probes known in the art. For example, module 30 may operate a magnetic-field based location tracking sub-system. (For simplicity components of such sub-system are not shown in FIG. 1.)

Alternatively or additionally, tracker module 30 may track probe 24 by measuring impedances between electrode 23, electrodes 29, and electrodes 22, as well as the impedances to other electrodes which may be located on the probe. (In this case electrodes 22 and/or electrodes 29 may provide both ECG and location tracking signals.) The Carto3® system, produced by Biosense-Webster (Irvine, Calif.), uses both magnetic field location tracking and impedance measurements for location tracking.

Using tracker module 30, processor 40 is able to measure locations of distal end 32. In addition, using both tracker module 30 and ECG module 36, the processor is able to measure locations of the distal end, as well as LATs of the actual electrical signals detected at these particular locations. As indicated above, electrical tracking signals from an individual electrode 22, can be integrated with the magnetic tracking signals so that the location of each electrode is recorded. Such hybrid (i.e., magnetic/electric) tracking system and method, named Advanced Current Location (ACL) is implemented in various medical applications, for example, in the CARTO™ system, produced by Biosense-Webster Inc., and is described in detail in U.S. Pat. No. 8,456,182 whose disclosure is incorporated herein by reference.

Results of the operations performed by processor 40 are presented to physician 28 on display 48, which typically presents a graphic user interface to the physician, a visual representation of the ECG signals sensed by electrodes 22, and/or an image or map of heart 34 while it is being investigated.

The software run by processor 40 may be downloaded to processor 40 in electronic form, over a network, for example, or it may, alternatively or additionally, be provided and/or stored on non-transitory tangible media, such as magnetic, optical, or electronic memory. In particular, processor 40 runs a dedicated algorithm that enables processor 40 to perform the disclosed steps, as described below.

Figure 2:
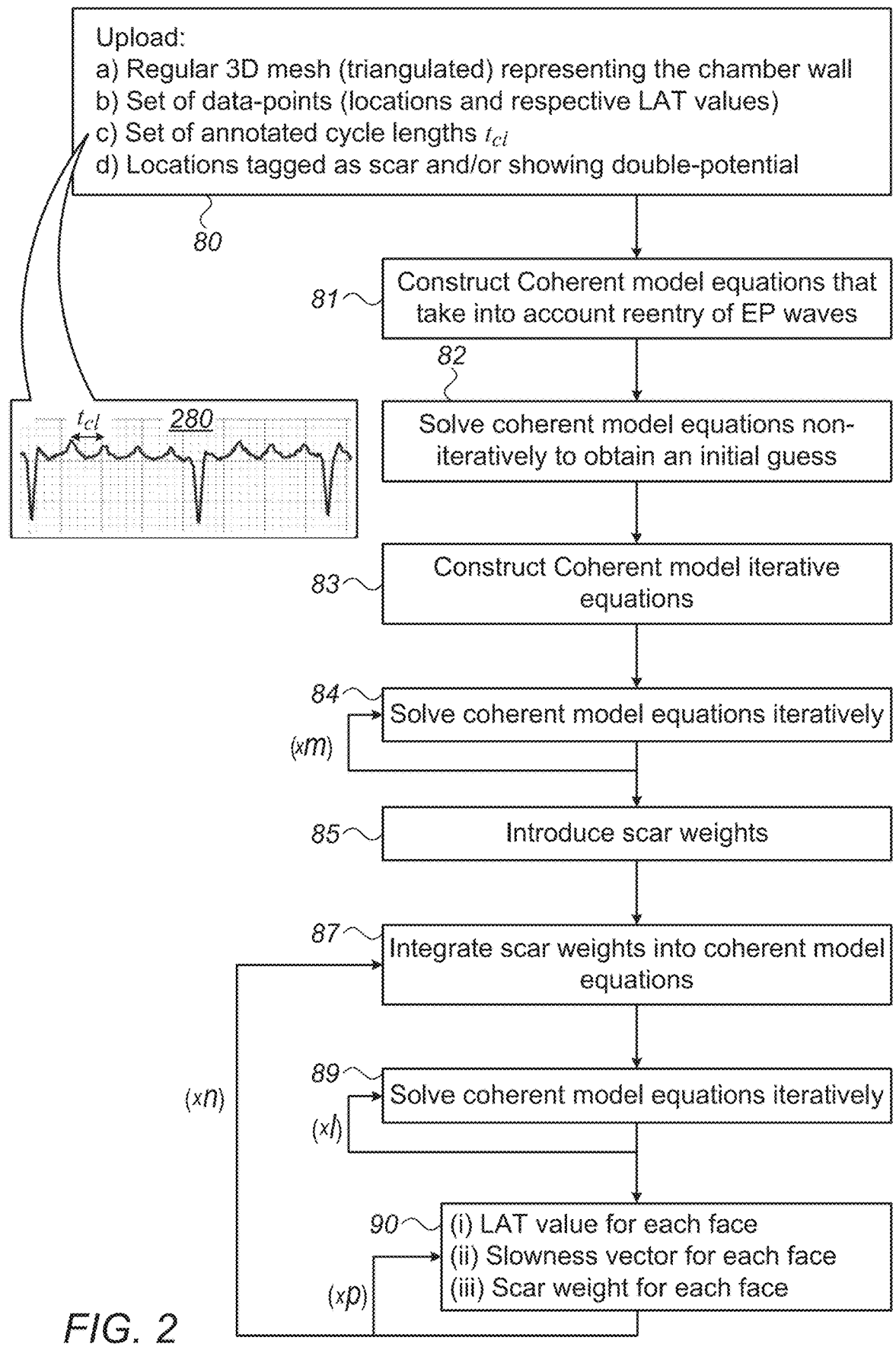
FIG. 2 is a flow chart that schematically illustrates a method and algorithm for calculating a coherent EP activation wave, in accordance with an embodiment of the present invention.

Iterative Coherent Mapping of Cardiac EP Activation Including Reentry and Scar Effects FIG. 2 is a flow chart that schematically illustrates a method and algorithm for calculating a coherent EP activation wave, in accordance with an embodiment of the present invention. The algorithm according to the present embodiment is carried out by processor 40.

A general description of steps 80-84 of the ICEA method now follows, before describing these steps in detail using the flow chart of FIG. 2. In some embodiments, the disclosed method includes receiving an input three-dimensional (3D) mesh (i.e., a shape) that may model, for example, an atrium of a heart. The 3D input mesh comprises polygons, such as triangles (i.e., a triangular mesh). In some embodiments of the present invention, a processor re-meshes the input mesh into a regular mesh comprising regular triangles (also named hereinafter "faces"). The regular mesh enables defining and iteratively solving a set of linear equations that maintain continuity of an EP wave, as well as reducing the computation effort, as described below.

The disclosed methods further include receiving a set of data points comprising measured locations over a wall tissue of the atrium and a respective set of local activation times (LAT) measured at the locations. In some embodiments, the set of data points is measured using a catheter-based electroanatomical mapping system, such as CARTO™, that uses a mapping catheter such as the PENTARAY® or the LASSO® (system and catheters are both made by Biosense-Webster, Irvine, Calif.).

In some embodiments, the disclosed methods use, as an input, an anatomical map obtained using Fast Anatomical Mapping (FAM) technique. The disclosed method may use more informative electro-anatomical maps as an input anatomical map, by processor 40 discarding any information in the map apart of the anatomy itself (e.g., what is used from the input electro-anatomical map of a cardiac chamber is the original mesh for a chamber geometry).

In some embodiments of the present invention, a processor either discards some of the received data points (i.e., measured locations and respective LAT) and/or performs data fitting to some of the data points so that the data points match the disclosed regular mesh.

In an embodiment, processor 40 discards data points that were determined as acquired while the mapping electrode was not in physical contact with the tissue, using a technique called Tissue Proximity Index (TPI).

In another embodiment, the processor adjusts measured positions which otherwise do not fit with a realistic description of an anatomy as provided by the regular mesh. In this way, the disclosed coherent mapping method overcomes errors in the catheter-measured locations, such as ones originating from the catheter applying force to the chamber wall and deforming the shape (force applied to ensure an EP signal acquiring electrode is in good electrical contact with the tissue), or from respiratory movement that is not related to the change of the catheter position on the chamber wall.

Next, the processor uses the inputs, i.e., the measured positions and respective LATs, and the input mesh re-meshed into triangular faces. In an embodiment, the disclosed model assumes that the propagation of an EP activation wave between two adjacent faces is in the direction of its slowness vectors, along a geodesic over the shape that connects the face centers. The time difference between face centers is thus the geodesic distance between them multiplied by the slowness vector.

The model initially further assumes that an EP activation wave is continuous, which means that neighboring faces should have similar slowness vectors. Moreover, the model also initially assumes that the conduction velocity of the EP activation waves is between a minimal and a maximal possible velocity (i.e., within a velocity range known for a normal heart muscle).

The disclosed model formulates the above assumptions into a set of linear equations under boundary conditions. A processor first solves the equations non-iteratively to obtain an initial guess of the coherent EP activation wave overlaid on the shape. The ICEA model may be recalculated based on accumulating supportive data, such as the local velocity vectors, to ensure that the EP activation map continues to change as data is collected. In an embodiment, the disclosed ICEA calculation is initiated by the user, usually after all the EP data was acquired. If new EP data is to be added, the user starts the calculation again from the very beginning, including the initial non-iterative solution.

Using the initial solution, the processor next iteratively solves the set of linear equations in a least-squares manner aimed at finding the "best-fit" EP activation, based on an additional assumption: that measured LAT values for each face influence their neighboring faces LAT values as a function of the distance from the measurement point to the neighboring face center. The iterative calculations yield in a global best-fit solution consisting of the derived EP activation wave overlaid on the shape. The number of iterations, which is typically up to several, is a preset parameter, which is based on visual inspection of numerous EA maps during a development phase, so as to confirm that there are no more apparent changes in the solution beyond a preset number of iterations. A user initiates the calculation and typically receives a complete ICEA map within several seconds.

The process begins at an uploading step 80, in which processor 40 uploads input for the method, the input including (i) 3D mesh (triangulated) representing the cardiac chamber wall, (ii) set of measured data-points (e.g., position and LAT), (iii) cycle lengths annotated in ECG traces, such as a cycle length, $t_{cl}$, of atrial flutter, shown in inset 280, and (iv), tagged locations such as scar and double potential. In some embodiments, steps (iii) or (iv) are not required, for example, in case the following calculation does not consider reentry, or does not include scar related calculations.

Next, at an equation construction step 81, processor 40 assigns two variables, an LAT value and slowness vector, for each face (i.e., triangle) in the mesh. To construct a set of equations for the two variables, the method makes three assumptions that affect the two variables:

1. That the EP activation wave is continuous, meaning that neighboring faces should have similar slowness vectors.

2. That a measured LAT value at a given face influences the calculated neighboring faces LAT as a function of the distance from the measurement location to the centroid of a neighboring face.

3. That the activation wave maintains the disclosed propagation equations, meaning that the wave propagates between faces in the direction of its slowness vectors, and the time difference between face centers is the geodesic distance between them multiplied by the slowness vector.

From the above assumptions into a set of linear equations is derived:

$$\begin{cases} w_{i,j}^{dist}(\varphi_i^{meas} - \varphi_j) = 0 & (I) \\ \vec{s}_i = R(j,i)\vec{s}_j & (II) \\ \vec{s}_j \cdot \vec{d}_j - \vec{s}_i \cdot \vec{d}_i = \varphi_j - \varphi_i & (III) \end{cases} \quad \text{Eq. 1}$$

where in Eq. 1(I), a weight $w_{i,j}^{dist}$, also named hereinafter "proximity weight," represents the relative effect a measured LAT value i has on a LAT value calculated for a face j, and $\varphi$ is periodic complex function representing a cyclic EP activation wave (to take account of reentries) having the looked-for LAT value as a variable.

In Eq. 1, eq. (I) relates the LAT measurement at face i to the LAT value of face j using $w_{i,j}^{dist}$, which is exponentially attenuated by the distance between any of the measurement locations used and the face location, to have decreasing influence with an increasing distance from the regular shape. As $w_{i,j}^{dist}$ is set to zero beyond a given distance, typically in the order of several millimeters, some of these equations are null expressions. Each EP measurement has, in this way, a relative effect that is proportional to its distance from the regular shape, and each measurement affects the neighboring faces. Measured points closest to a regular shape are more likely to be accurate.

Eq. (II) connects slowness vectors $\vec{s}_i$ and $\vec{s}_j$, which are given in complex numbers to handle reentry, as described below, by a rotation matrix R(j,i).

Eq. (III) is a propagation equation that states that a wave propagating between two adjacent faces should have slowness and LATs that are related by the distances between the associated faces. As the equation will be written for any two adjacent faces, it reflects the relation between all the LATs and slowness vectors associated with all the faces in the shape.

Eq. 1(I)-(III) apply relations:

$$\begin{cases} \vec{\tilde{s}}_i = \frac{2\pi i}{T_{cl}} \varphi_i \vec{s}_i \\ \varphi_i = \exp\left(2\pi i \frac{t_i}{T_{cl}}\right) \end{cases} \quad \text{Eq. 2}$$

The relations of Eq. 2 assume that all time scales are short $$\frac{t_0 - t_i}{T_{cl}}, \frac{t_j - t_0}{T_{Cl}} << 1,$$

and that the assumptions Sin(x)≈x and Cos(x)≈1 hold. $T_{cl}$ in Eq. 2 is a reentry cycle length.

The above cyclic wave complex number format as a function of time takes account of the above described occurrence of reentry cases, in which the activation wave continuously propagates at some cycle length.

Eq. 1(II) is a continuous propagation equation (similarity), in which two adjacent faces are required to have similar slowness vectors $\vec{s}_i$. Slowness vectors $\vec{s}_i$ are in $\mathbb{C}^3$. R(j,i) is a rotation matrix between two neighboring faces I and J.

Eq. 1(III) is a propagation equation of the cyclic EP activation wave between faces. The distance that the wave front has travelled is a projection of the geodesic distance which is the distance between the two faces centroids, $\|\vec{d}_j\| + \|\vec{d}_i\|$.

At an initial equation solving step 82, processor 40 solves Eq. 1 non-iteratively to obtain an initial guess of the EP activation wave. In an embodiment, Eq. 1 is solved in a least squares manner. The solution is performed using mathematical methods from numerical linear algebra comprising Cholesky decomposition followed by forward and backward substitution, as described in the book "Numerical Linear Algebra," by Trefethen, L. N., and Bau, D. (1997), pages 172-178, published by SIAM publishing house.

In an embodiment, terms (I) (II) (III) of Eq. 1 are incorporated into a single sparse matrix equation. Each sub-equation (i.e., term) can be assigned a different optimization-weight to balance the various influencing factors. These optimization-weights can be varied between iterations. These optimization-weights are also preset parameters like the number of iterations.

In the initial guess, the physical meaning of the slowness vector describes the change of the complex phase of time with distance. This is in contrast to the regular slowness vector which describes the change of time with distance. As the slowness is complex, the physical definition is different and somewhat artificial.

Solving Eq. 1 in the complex domain addresses cyclic activation in a natural way, and removes the complications imposed by the early-meets-late effect. To obtain a physically meaningful expression for the slowness additional steps are required, in which iterative set of equation is constructed and solved.

Note that solving complex functions enables simple calculation of cyclic activation but requires the conversion of complex slowness back to real values in order to retain the physical meaning of the slowness vector. Thus, finally, $\vec{s}_l$ is converted back to $\vec{s}_l \in \mathbb{R}^3$. This is done by using Eq. 1 in terms of real variables $\vec{s}_l$, $\mathrm{Re}(\varphi_i)$, $\mathrm{Im}(\varphi_i)$.

At an iterative equations construction step 83, to iteratively solve Eq. 1 using the initial guess obtained in step 82, the disclosed method linearizes Eq. 1 using for $\vec{s}_l$, $\varphi_i$:

$$\begin{cases} \varphi_i = \varphi_i^{n-1} + \Delta \varphi_i \\ \vec{s}_l = \vec{s}_l^{n-1} + \Delta \vec{s}_l \end{cases} \qquad \text{Eq. 3}$$

To receive Linearized Eq. 1:

$$\begin{cases} w_{i,j}^{dist}(Re(\varphi_i^{meas}) - Re(\varphi_j) - Re(\Delta\varphi_j)) = 0 & \text{Eq. 4. (I)} \\ w_{i,j}^{dist}(Re(\varphi_i^{meas}) - Im(\varphi_j) - Im(\Delta\varphi_j)) = 0 \end{cases}$$

$$\vec{s}_i^{n-1} + \Delta\vec{s}_l = R(j,i)(\vec{s}_j^{n-1} + \Delta\vec{s}_j) \qquad \text{Eq. 4. (II)}$$

$$(\vec{s}_j^{n-1} + \Delta\vec{s}_j)\cdot \vec{d}_j \mathrm{Im}(\varphi_j^{n-1}) - (\vec{s}_i^{n-1} + \Delta\vec{s}_l)\cdot \vec{d}_l \mathrm{Im}(\varphi_i^{n-1}) + \qquad \text{Eq. 4. (III)}$$
$$\vec{s}_j^{n-1}\cdot \vec{d}_j \mathrm{Im}(\Delta\varphi_j) - \vec{s}_i^{n-1}\cdot \vec{d}_l \mathrm{Im}(\Delta\varphi_i) =$$
$$-\frac{T_{cl}}{2\pi} \mathrm{Re}(\varphi_j^{n-1} + \Delta\varphi_j - (\varphi_i^{n-1} + \Delta\varphi_i))$$

In an embodiment, real linearized Eq. 1, i.e., Eq. 4, is solved for the linear variables $\Delta\varphi_i$, $\Delta\vec{s}_l$. The constants $\varphi_i^{n-1}$, $\vec{s}_i^{n-1}$ are the solutions obtained in the previous iteration. In the first iteration, $\varphi_i^0$, $\vec{s}_i^0$ are initialized by the solutions for the complex LAT and real slowness of the initial guess obtained in step 82.

Conduction velocities for each face are calculated based on the measured activation time, the calculated vector of propagation, and known distance between the centers of each face. Under several conditions the linear solution might generate regions of near-zero slowness vectors (also named "sources" or "sinks"). Such regions are not realistic since they imply locations with infinite velocity. To maintain EP conduction velocities to be close to some positive physiological constant $\alpha$, a constraint is added:

$$\frac{1}{\|\vec{s}_l\|} = \frac{1}{a} \qquad \text{Eq. 5}$$

Eq. 5 "punishes" deviations of large velocities (small slowness) from $\alpha$. After a Taylor expansion the following set of constrains over $\Delta\vec{s}_l$, $\Delta\varphi_i$ is obtained:

$$\begin{cases} \|\vec{s}_i^{n-1}\| + \dfrac{\vec{s}_i^{n-1}\cdot \Delta\vec{s}_l}{\|\vec{s}_i^{n-1}\|} = a \\ \dfrac{1}{\|\vec{s}_i^{n-1}\|} - \dfrac{\vec{s}_i^{n-1}\cdot \Delta\vec{s}_l}{\|\vec{s}_i^{n-1}\|^3} = \dfrac{1}{a} \end{cases} \qquad \text{Eq. 6}$$

The constraints by Eq. 6 are added only after the linear initial solution is found, since it is not possible to write the constraints in linear form in $\vec{s}_l$ because it contains expressions with square roots such as $\|\vec{s}_l\|$, $$\frac{1}{\|\vec{s}_l\|}.$$

When writing the equations in delta form, it is possible to Taylor expand in $\Delta\vec{s}_l$ and write the constraints in linear form.

Next, at an iterative solving step 84, processor 40 solves Eq. 4 with variables $\mathrm{Re}(\Delta\varphi_i)$, $\mathrm{Im}(\Delta\varphi_i)$, $\Delta\vec{s}_l$ by first projecting the slowness onto the surface of the reconstruction and writing the equations in matrix form using the methods described in step 82 (i.e., changing a linear basis to one with which Eq. 4 is more easily solved).

In steps 81-84, Eq. 4 is solved assuming continuous propagation of the activation wave. To incorporate scar information into the solution, a framework is required to detect scars and allow the EP activation wave (i.e., the solution) to develop discontinuities in lines of block and non-conducting areas.

The disclosed coherent mapping method assigns smaller weights for constraints that make the solution incoherent (i.e., inconsistent or discontinuous). Thus, measured LAT values that the processor determines are invalid (i.e., outlier LAT values) are removed by the processor during iterations. The method assigns new weights after receiving a solution vector of an iteration. For LAT constraints this process filters out inconsistent points. For a neighbor's constraints this removes inconsistent edges.

A general description of steps 85-90 of the ICEA method now follows, before describing these steps in detail using the flow chart of FIG. 2. The framework is also built upon the iterative method, yet this time scar (face) weights, $w_i^{sf}$ are introduced, at a scar weight introduction step 85, and iteratively calculated in steps 87-100. The weights are in the range [0.05,1], where 0.05 indicates a scar.

The iteratively calculated weights infer data that increase or decrease the likelihood that a certain face is a scar and outputs calculated scar probabilities for each face. The scar weights (i.e., scar probabilities) $w_i^{sf}$ are then incorporated back in step 87 as multiplication weights that reduce the strength of the continuity equations in line of block regions. Constraints over the slowness norms, such as those set by Eq. 6, are reduced, as well, by the multiplication weights. This allows the solution to change more freely in line of block regions.

First, propagation equation Eq. 4(II) is multiplied by the minimum of the two respective weights $w_{ij}^{sf} = \min\{w_i^{sf}, w_j^{sf}\}$. for two faces neighboring an edge (i,j):

$$\vec{s}_i^{n-1} + \Delta\vec{s}_l = w_{ij}^{sf}\cdot R(j,i)(\vec{s}_j^{n-1} + \Delta\vec{s}_j) \qquad \text{Eq. 7}$$

This reflects the assumption that a slow conduction between the faces if any of them is in already indicated as a scar (i.e. having small $w_i^{sf}$).

Thus, for regions in which a scar is detected, weights of the continuous propagation equations 40 (II) are reduced. This reduces the requirement for slowness similarity between neighboring faces, allowing for a discontinuity in the wave propagation in regions with scars.

Second, the normalized slowness and velocity equations (Eq. 6) are multiplied with the calculated weights. Thus, reducing the requirement for a certain target velocity size for scar faces:

$$\begin{cases} \|\vec{s}_i^{n-1}\| + \dfrac{\vec{s}_i^{n-1} \cdot \Delta \vec{s_i}}{\|\vec{s}_i^{n-1}\|} = a \cdot w_i^{sf} \\ \dfrac{1}{\|\vec{s}_i^{n-1}\|} - \dfrac{\vec{s}_i^{n-1} \cdot \Delta \vec{s_i}}{\|\vec{s}_i^{n-1}\|^3} = \dfrac{1}{a \cdot w_i^{sf}} \end{cases} \quad \text{Eq. 8}$$

After the scar probabilities are integrated back into the equations, at a scar weight integration step 87, processor 40 resolves modified Eq. 4 and a new solution is proposed, in an LAT and slowness outputting step 89. Next, new, refined scar probabilities are calculated at step 100, up to a preset number of iterations that are verified to yield a sufficiently accurate map, such as the coherent EP activation map described in FIG. 6.

Figure 3:
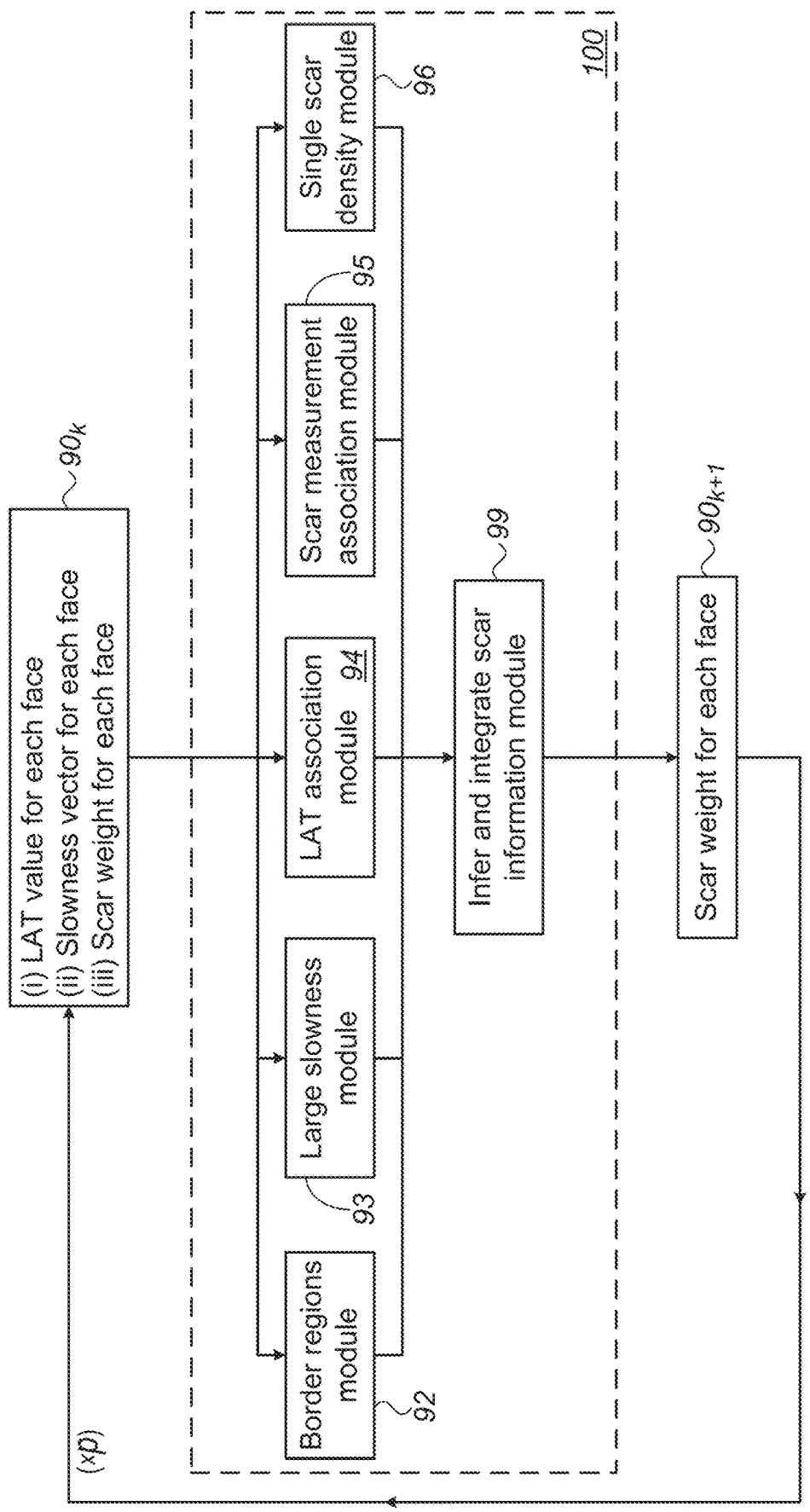
FIG. 3 is flow chart that schematically illustrates a method and algorithm for calculating scar probabilities as part of the process described in FIG. 2, in accordance with an embodiment of the present invention.

FIG. 3 is flow chart that schematically illustrates a method and algorithm for calculating scar probabilities as part of the process described in FIG. 2, in accordance with an embodiment of the present invention. FIG. 3 describes the different modules (i.e., calculation sub-steps) included in step 100, which allow an EP activation wave solution to develop discontinuities in lines of block and non-conducting areas. The algorithm according to the present embodiment is carried out by processor 40.

Step 100 includes calculation module (i.e., steps) 91-98 that infer data per each face that that increase or decrease the likelihood that a certain triangular face of the mesh represents a scar. The output of each of steps 91-98 is a weight ranging between zero and one. The weights are in the range [0,1], where one indicates a normal face, and zero indicates a scar or "slowly conductive" face (in the current version there is no differentiation between the two).

The weights calculated in steps 92-96 are arranged in a matrix form of a cost function, as described below, and step 99 calculates car weights $w_i^{sf}$ by minimizing the cost function. In step 99 processor 40 calculates the scar weights $w_i^{sf}$ by integrating the information collected in steps 91-98 into a combined probability for each face.

At a border region weighting step 92, processor 40 calculates a border region face weight $w_i^{frf}$ which indicate a slope of the dispersion of LATs from nearby measurements. A steep dispersion may indicate regions that border a scar.

At a large slowness weighting step 93, processor 40 calculates a slowness weight $w_i^{sl}$ which indicates if a face has a large slowness vector. This increases the probability of the face being a scar.

At an LAT association weighting step 94, processor 40 weighs a difference between a measured LAT and the calculated face LAT. This is called the measurement face weight and is denoted $w_{i,j}^{mf}$. The weight $w_{i,j}^{mf}$ reflects the "link strength" between a measurement point i and a face j.

At a scar association weighting step 95, processor 40 calculates a weight $w_{i,j}^{smf}$ that reflects the "link strength" between a scar measurement point i and a face j. The weight decreases with increased spatial distance between face i and a face j.

At a singleton scar density weighting step 96, processor 40 calculates a singleton scar density weight $w_i^{ssd}$ which indicates a region where a single scar measurement is surrounded by regular (non-scar) measurements. The weight is defined to reduce the scar probability for any face where the scar indication is too sparse to realistically be a valid measurement. This is done by looking at the ratio between nearby scar measurements and nearby non-scar measurements. If there are many non-scar measurements and an isolated scar measurement, the weight generated from this module decreases the probability of this face is a scar.

The different weights calculated in steps 92-96 are processed by an infer integrate scar info module 99 which calculates scar probabilities for each face. As FIG. 2 shows, the scar probabilities are then incorporated back into step 87 of the iterative calculation to reduce the strength of the continuity equations in line of block regions. Furthermore, the relative strength of the slowness norm and velocity norm equations are also reduced, as noted above. This allows the solution to change more freely in line of block regions.

Step 99 calculates a scar probability weight for each face by formulating into a cost function the following rules:
1. Scars/slow conductive areas are continuous.
2. A scar tagged measurement means that there is a scar nearby.
3. Areas with many nearby measurement points are conductive.
4. A large border region weight or double potential tagged measurements indicate the border of a scar.
5. Areas with low surrounding information, namely, with no measurement points nearby, have a larger probability of being a scar.
6. Areas which are in close proximity to both a scar tagged measurement and have a large slowness, have a larger probability of being a scar.

The resulting cost is defined as the sum of a quadratic term and a linear term:

$$C(w_i^{sf}) = \dfrac{(w_i^{sf})^t H w_j^{sf}}{2} + (w_i^{sf})^T L \quad \text{Eq. 9}$$

where $w_i^{sf}$ is the vector of weights for all faces, and H(i,j) H is a symmetric matrix of cost terms involving pairs of face weights:

$$H_{nm}(i,j) = \begin{cases} 1 & n = m = i \text{ or } n = m = j \\ -1 & n = i, m = j \text{ or } n = j, m = i \\ 0 & \text{else} \end{cases} \quad \text{Eq. 10}$$

A quadratic cost term of Eq. 9 is defined as:

$$C_{quadratic} = (w_i^{sf})^t H(i,j)(w_j^{sf}) = (w_i^{sf} - w_j^{sf})^2 \quad \text{Eq. 11}$$

H reflects a continuity of scar probabilities, meaning that neighboring faces should have similar scar probabilities. This is aimed at connecting fragmented scar regions.

L is a vector of linear cost term associates to each face. It is composed of two contradicting terms, one term which includes all information that supports a scar, while the other includes all information indicating a normal face:

The linear cost vector is then defined as $$L_i = f \cdot S_i^{scar} - (1-f) \cdot S_i^{normal} \quad \text{Eq. 12}$$

The linear terms $S_i^{scar}$, $S_i^{normal}$ for each face either support the existence of a scar face or a normal face and are functions of the weights calculated in steps 92-96. f is a normalizing factor with values between [0-1]. When the cost function is positive for a face i, this means the scores indicate a scar, and processor 40 acts to minimize the score by assigning a low weight to that face. When the cost function is negative, this indicates a normal face and processor 40 acts to maximize the weight by assigning a high weight to that face. This is done by writing the linear cost term as:

$$C_{linear} = (w^{sf})^t L \quad \text{Eq. 13}$$

This term will be added to the quadratic term (Eq. 11) to obtain the final cost function. The optimizer solver for weights $w^{sf}$ defined for each face. Where a $w^{sf}$ weight of one indicates a conductive face while a weight of zero indicates a block.

For example, assuming f is 0.5, if $S_i^{scar}$ is 1 and $S_i^{normal}$ is 0.2, which are the scar and normal scores for the face, $L_i$ will be 0.4 which is greater than zero. This encourages the optimizer to give a $w^{sf}$ weight that is close to zero for this face in order to minimize the total cost function. A $w^{sf}$ weight close to zero indicates a scar. On the opposite case that $S_i^{scar}$ is 0 and $S_i^{normal}$ is 1 then $L_i = -1$, which gives a negative cost function that forces the optimizer assigning a $w^{sf}$ close to 1, which indicates a normal face. The use of negative and positive values allows the optimizer to assign values close to 1 for faces which are normal while assigning values close to 0 for scarred faces.

Processor 40 derives the weights of vector $w_i^{sf}$ by minimizing the total cost function $C(w_i^{sf})$, which is done using quadratic programing. We formulate the problem as follows:

$$\underset{w_i^{sf}}{\arg\min} \ C(w_i^{sf}), \ \text{st.} \ 0.05 \le w_i^{sf} \le 1$$

This problem is solved using an interior point convex optimization, as described by Florian A. Potra and Stephen J. Wright in, "Interior-point methods," Journal of Computational and Applied Mathematics, Volume 124, issues (1-2), pages 281-302, (2000). The output of this module are the scar face weights $w_i^{sf}$ which is the probability that face i is normal incorporated into step 87.

The example flow chart shown in FIG. 3 is chosen purely for the sake of conceptual clarity. For example, further implementation details are omitted for the simplicity of presentation.

Figure 4:
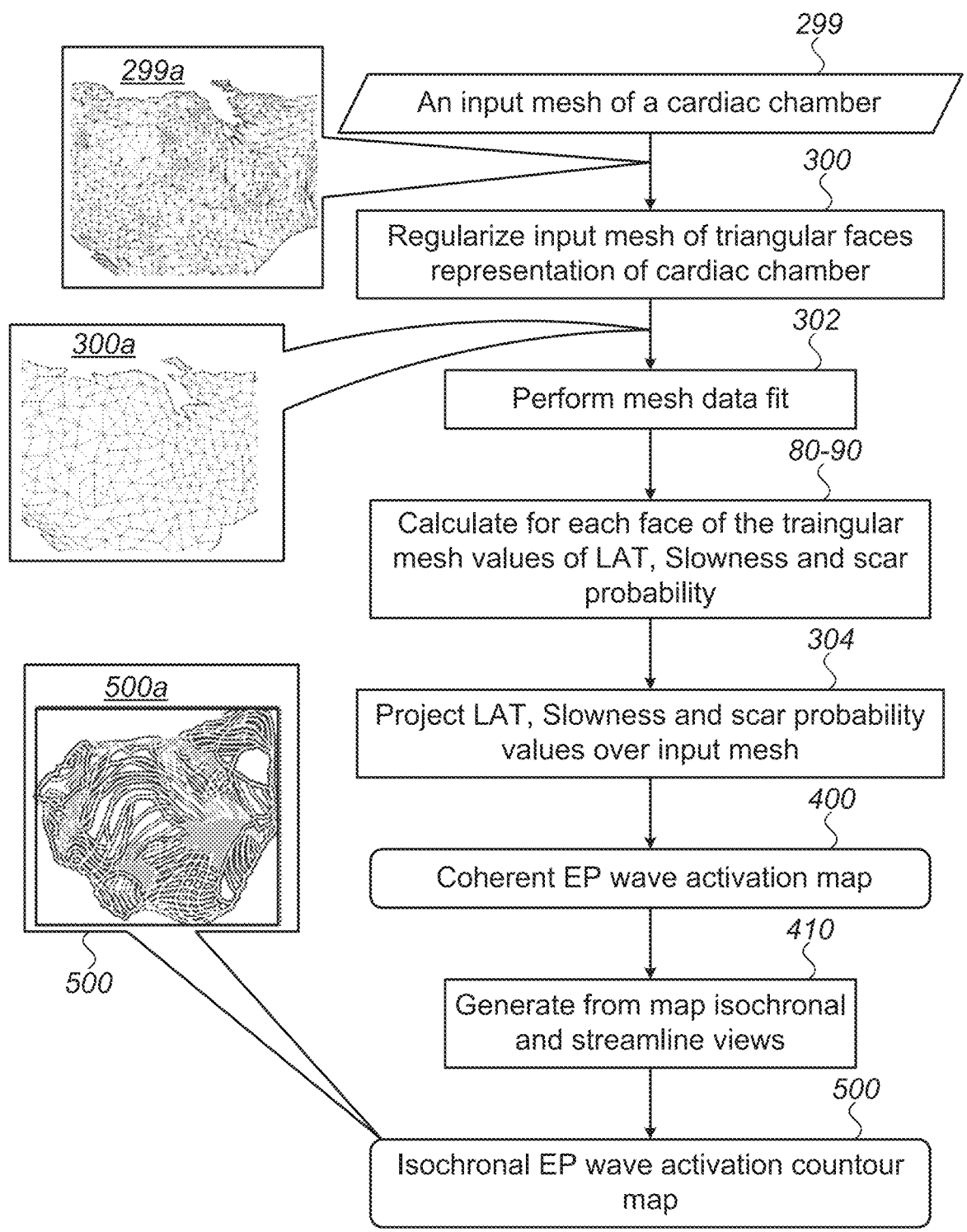
FIG. 4 is flow chart that schematically illustrates a method and algorithm for generating an EP activation wave map from the process described in FIG. 2, in accordance with an embodiment of the present invention.

FIG. 4 is flow chart that schematically illustrates a method and algorithm for generating an EP activation wave map from the process described in FIG. 2, in accordance with an embodiment of the present invention. The algorithm according to the present embodiment carries out a process that begins with processor 40 receiving a three-dimensional mesh representation 299a of a cardiac chamber, at a receiving input mesh step 299. As seen, mesh 299aa comprises irregular triangular faces. A mesh such as mesh 299a, with triangles that have large and small sides, which is typically generated by the aforementioned FAM technique, causes errors in the geometric approximations made by the disclosed method. Next, at an input mesh regularization step 300, processor 40 re-meshes input mesh 299 to produce a more regular mesh 300a. The re-meshing is performed also for optimizing the calculations steps applied by the disclosed method to the EP wave estimation needs. In an embodiment, the mesh resolution (number of triangles) determines the number of generated equations (e.g., as implemented in a given size of matrices). Step 300 reduces the computation effort described in FIGS. 2 and 3 by reducing that number of equations.

Next, at a mesh data fit step 302, processor 40 virtually translates a fraction of the triangle centers to better fit nearby measured locations while holding the reconstruction intact. Step 302 is required, since, during data acquisition when the mesh is created, the mapping catheter tends to push the atria walls generating "inflated" reconstruction geometry. Many of the measurements are distant from the reconstruction, which adds uncertainty in associating the measurement location to the chamber geometry.

Next, processor 40 performs the calculations described in FIG. 2 and FIG. 3, using the dedicated algorithm, to derive, for each face of the optimized triangular mesh values of LAT, slowness, and scar probability, at the interactive calculation step 90. Typically, the scar weights are not updated every time LAT and slowness values are updated.

Then, at a projection step 304, processor 40 projects the resulting values of step 302 on the original mesh 299a. As described above, the EP activation wave is computed over a simplified mesh. Yet, the disclosed method provides a resulting coherent map for the original mesh. The map is defined in each center of a face for the low-resolution mesh. Processor 40 maps the high-resolution map faces (i.e., of input map 299a) to a point on the low-resolution mesh by shooting a ray from the high-resolution mesh in the direction of the normal to the face, inwards and outwards.

If only one ray hits the low-resolution mesh, processor 40 chooses that point as the associated point on the low-resolution mesh. If the rays in both directions hit the mesh, processor 40 chooses the closest point.

Then, processor 40 interpolates the LAT value inside the face of the low-resolution mesh at the point hit by the ray and assigns this value to the face of the high-resolution mesh. In an embodiment, processor 40 omits LAT information in tissue regions where the number of acquired data points is smaller than a given required value. Such tissue region, in which EP mapping yields too sparse mapping, are therefore "greyed out" in any resulting visualization.

Figure 6:
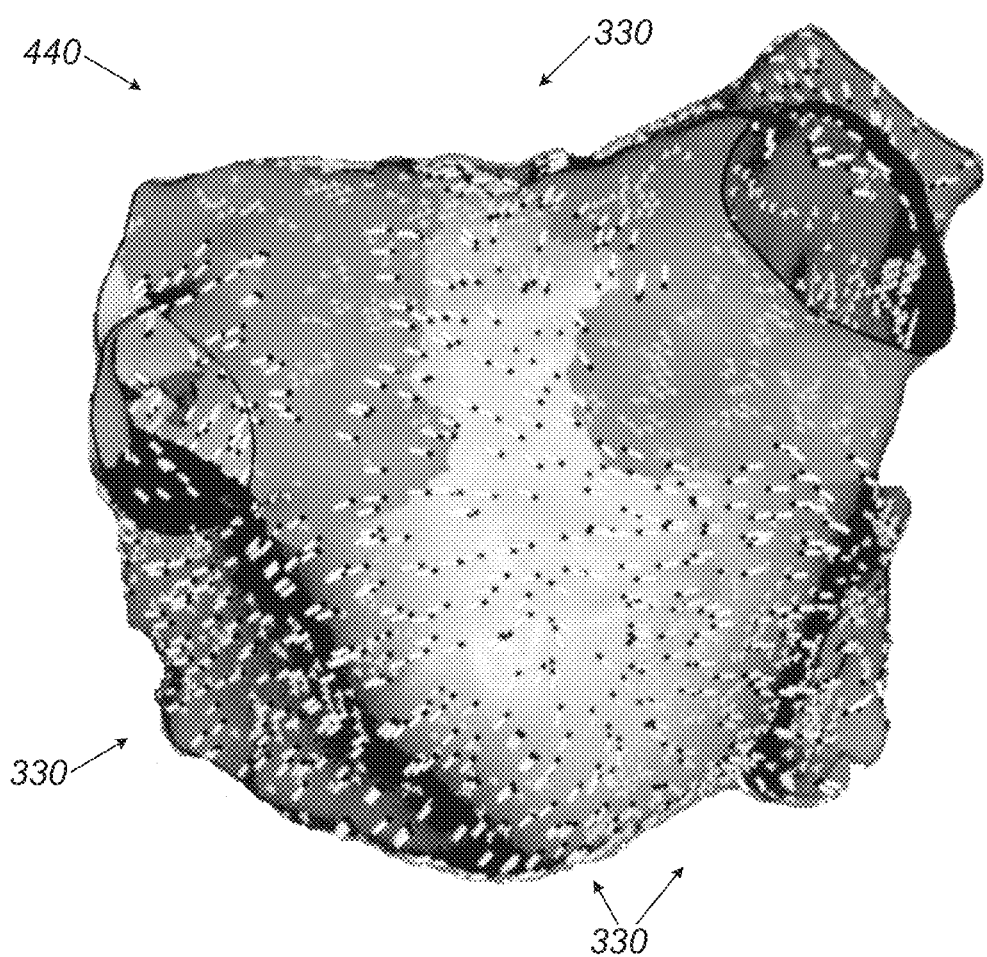
FIG. 6 is a schematic, pictorial volume rendering of a coherent EP activation map of a left atrium overlaid with conduction arrows that illustrate the propagation of the EP activation wave, in accordance with an embodiment of the present invention.

Step 304 results in processor 40 producing a coherent EP activation wave map 400, which is described in FIG. 6.

A key step towards understanding an arrhythmic flutter is the ability to view a wave cycle over an entire mesh. Visualization of 3D meshes in 2D screens incorporates some difficulties, including, the view of the back side of the mesh, deciding frontal versus distal parts of the mesh, and others. At an isochronal view generation step 410, processor 40 image-processes map 400 into an isochronal view 500.

Isochronal view 500 is a contour map 500a where each contour line is a curve along which the LAT is constant. Isochronal view 500a is brought by way of example of a left atrium in anterior-posterior (AP) view. In practice the map is color coded.

Map 500a is transparent, which allows the user to view the entire span of a wave's cycle in one view, while the front and distant components are easily distinguished. Furthermore, the view makes it easy to follow the cycle around the entire structure, leading to a better understanding of the arrhythmia. The propagation speed of the wave is apparent by the density of the curves because the contour interval is evenly spaced in time. A region with a high density of contours represents slow propagation, and a low density represents fast propagation. Scar regions are seen as uniform areas that lack contours.

The example flow chart shown in FIG. 4 is chosen purely for the sake of conceptual clarity. For example, illustrative graphical outputs of some steps, such as step 302, are omitted for the simplicity of presentation.

Figure 5:
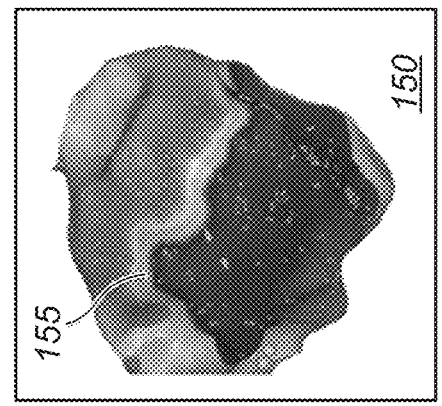
FIG. 5 is a schematic, pictorial volume rendering of a coherent EP activation map of a left atrium that takes account of into account reentry of EP waves and scar tissue, in accordance with an embodiment of the present invention.
Figure 5:
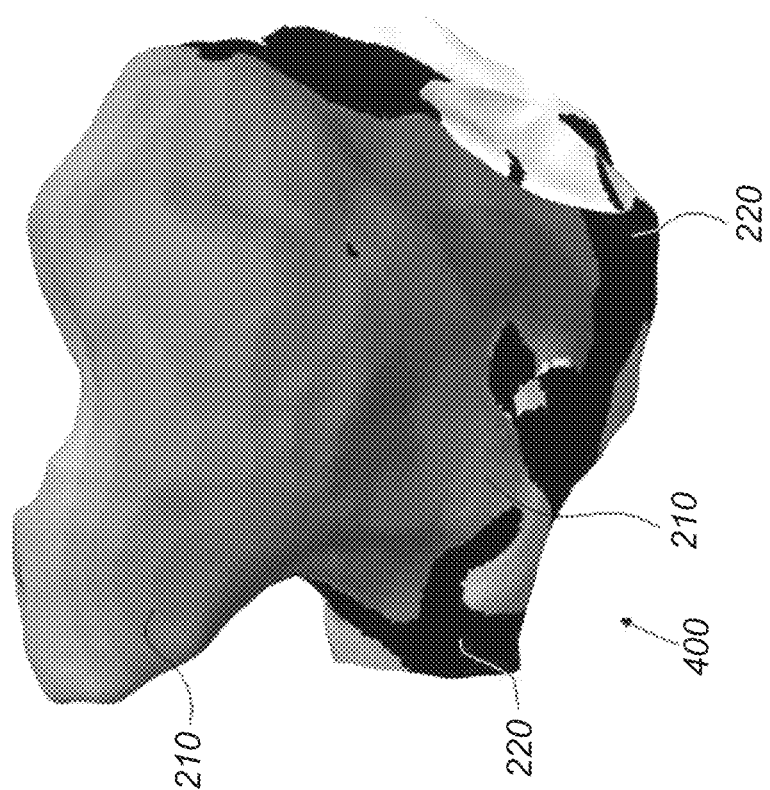

FIG. 5 is a schematic, pictorial volume rendering of a coherent EP activation map 400 of a left atrium that takes account of reentry of EP waves and of scar tissue, in accordance with an embodiment of the present invention. As seen, map 400 shows a realistic, continuous EP activation pattern at regions 210, as the above described rainbow artifact is suppressed by the disclosed method. The discontinuities that are evident are between EP conducting regions 210 and non-conducting scar regions 220, as expected.

Inset 150 of FIG. 5 is a volume rendering of an interpolation of a color representation of an EP activation over a left atrium, calculated without the disclosed technique, for reference purposes. The example shown in inset 150 does not take wave reentry into account. As a result, and as seen in the inset, a "rainbow" artifact 155 appears. In the example shown in the inset, an EP wave propagation over the chamber spans an entire reentry cycle, where a wavefront "late" in the cycle meets the "early" wavefront of the next cycle. In this example, tissue regions are assigned LATs that are one cycle length apart. A narrow multi-shade path, rainbow like, which, when color coded, indicates a transition of one full cycle length between neighboring regions, thus causes a discontinuity in the map that embodiments of present invention eliminate, as explained above. Namely, the above described rainbow artifact is eliminated entirely using the disclosed ICEA method.

In some embodiments, a cyclic color scale is used to eliminate dependency on "Early Meets Late" in window of interest (WOI). The colors represent the relative time differences, in relation to a reference electrogram, eliminating the concept of "early meets late." The color circle represents the activation pattern. Thus, for example, a red color does not represent early and a purple color does not represent late, as they do in a standard map; the color circle describes the proportional relationship in activation time in a natural, cyclic manner that does not create the rainbow-like transitions.

FIG. 6 is a schematic, pictorial volume rendering of a coherent EP activation map 440 of a left atrium overlaid with conduction arrows 330 that illustrate the propagation of the EP activation wave, in accordance with an embodiment of the present invention. Conduction arrows 330 are vectors, all with a fixed length, and each with a direction of a respective slowness vector at the location over the shape which provide additional visualization of the EP activity. For example, conduction arrows 330 are typically seen as encircling a scar region. In another embodiment (not shown in FIG. 6), the conduction arrows have different lengths that represent the size of the slowness in addition to its direction.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
receiving an input mesh representation of a cardiac chamber, a set of measured locations on a wall tissue of the cardiac chamber, and a respective set of local activation times (LATs) measured at the locations;
re-meshing the input mesh into a regular mesh comprising regularized polygons;
data fitting the set of measured locations and respective LATs to the regularized polygons;
iteratively calculating for the regularized polygons respective LAT values, so as to obtain a cyclic EP activation wave solution over the regular mesh that take account of reentry of an EP wave, wherein iteratively calculating the LAT values comprises iteratively solving a set of complex valued equations that are configured to describe the reentry of an EP wave by including a reentry cycle length value; and
presenting an electroanatomical map comprising the cyclic EP activation wave overlaid on the regular mesh.

2. The method according to claim 1, wherein iteratively calculating the LAT values comprises iteratively solving a set of three linear equations for the LAT values, slowness values and propagation of the EP wave.

3. The method according to claim 1, wherein iteratively calculating the LAT values comprises reassigning to each regularized polygon a slowness vector recalculated using a proximity weight multiplier.

4. A system, comprising:
an interface, which is configured to receive an input mesh representation of a cardiac chamber, a set of measured locations on a wall tissue of the cardiac chamber and a respective set of local activation times (LAT) measured at the locations; and
a processor, which is configured to:
re-mesh the input mesh into a regular mesh comprising regularized polygons; data fit the set of measured locations and respective LATs to the regularized polygons;
iteratively calculate for the regularized polygons respective LAT values, so as to obtain a cyclic EP activation wave solution over the regular mesh that take account of reentry of an EP wave, wherein the processor is configured to iteratively calculate the LAT values by iteratively solving a set of complex valued equations that are configured to describe the reentry of an EP wave by including a reentry cycle length value; and
present an electroanatomical map comprising the cyclic EP activation wave overlaid on the regular mesh.

5. The system according to claim 4, wherein the processor is configured to iteratively calculate the LAT values by iteratively solving a set of three linear equations for the LAT values, slowness values and propagation of the EP wave.

6. The system according to claim 5, wherein the processor is configured to iteratively calculate the LAT values by reassigning to each regularized polygon a slowness vector recalculated using a proximity weight multiplier.

* * * * *